United States Patent [19]

Li

[11] 4,168,246
[45] Sep. 18, 1979

[54] PRODUCTION OF (AMM)OXIDATION CATALYST

[75] Inventor: Tao P. Li, Chesterfield, Mo.

[73] Assignee: Monsanto Company, St. Louis, Mo.

[21] Appl. No.: 813,716

[22] Filed: Jul. 7, 1977

Related U.S. Application Data

[63] Continuation-in-part of Ser. No. 636,011, Nov. 28, 1975, Pat. No. 4,040,978.

[51] Int. Cl.$^2$ .................. B01J 27/14; B01J 29/16; B01J 23/84; C07C 120/02
[52] U.S. Cl. .................. 252/437; 252/456; 252/470; 260/465.3
[58] Field of Search .................. 252/437, 456, 470

[56] References Cited

U.S. PATENT DOCUMENTS

| | | | |
|---|---|---|---|
| 3,347,899 | 10/1967 | Caponali et al. | 252/470 X |
| 3,471,556 | 10/1969 | Yamaguchi et al. | 260/530 N |
| 3,766,092 | 10/1973 | Honda et al. | 252/437 |
| 3,778,386 | 12/1973 | Takenaka et al. | 252/432 |
| 3,836,586 | 9/1974 | Yamada et al. | 252/470 X |
| 3,882,159 | 5/1975 | Callahan et al. | 260/533 N X |
| 3,984,477 | 10/1976 | Kudo et al. | 252/470 X |
| 3,985,800 | 10/1976 | Erpenbach et al. | 252/470 X |
| 4,001,317 | 1/1977 | Grasselli et al. | 252/470 X |
| 4,034,008 | 7/1977 | Kurtz et al. | 252/456 X |
| 4,040,978 | 8/1977 | Li | 252/437 |
| 4,052,333 | 10/1977 | Lee | 252/437 X |

*Primary Examiner*—Delbert E. Gantz
*Assistant Examiner*—William G. Wright
*Attorney, Agent, or Firm*—James C. Logomasini; Paul L. Passley; Neal E. Willis

[57] ABSTRACT

An (amm)oxidation catalyst is made by forming an aqueous slurry containing the molybdate of at least one of the elements in the group consisting of cobalt, nickel and iron, a bismuth oxide or salt, and optionally a phosphate radical and an ion of an element selected from the group consisting of sodium, potassium and calcium, and thereafter separating the solid phase from the slurry and calcining said solid phase to form the catalyst.

9 Claims, No Drawings

4,168,246

PRODUCTION OF (AMM)OXIDATION CATALYST

CROSS REFERENCE TO RELATED APPLICATIONS

This application is a continuation-in-part of my co-pending U.S. application Ser. No. 636,011 now U.S. Pat. No. 4,040,978.

BACKGROUND OF THE INVENTION

This invention relates to an oxidation and/or ammoxidation catalyst containing the elements molybdenum, bismuth, one or more elements selected from iron, nickel and cobalt, and, optionally phosphorus and an alkali metal selected from sodium and potassium.

It is well known that olefins can be oxidized to oxygenated hydrocarbons such as unsaturated aldehydes and acids, for example, acrolein and methacrolein, and acrylic and methacrylic acid. It is also well known that olefins can be ammoxidized to unsaturated nitriles such as acrylonitrile and methacrylonitrile. The value of such oxygenated hydrocarbons and unsaturated nitriles is generally well recognized with acrylonitrile being among the most valuable monomers available to the polymer industry for producing useful polymeric products.

Various catalytic processes are known for the oxidation and/or ammoxidation of olefins. Such processes commonly react an olefin or an olefin-ammonia mixture with oxygen in the vapor phase in the presence of a catalyst. For the production of acrolein and acrylonitrile, propylene is the generally used olefin reactant and for the production of methacrolein and methacrylonitrile, isobutylene is the generally used olefin reactant.

Catalysts disclosed as having significant utility in such (amm)oxidation processes are described in U.S. Pat. No. 3,882,159 and Example III of U.S. Pat. No. 3,746,657 describes such a catalyst containing the elements molybdenum, potassium, phosphorus, cobalt, iron, nickel, bismuth and oxygen deposited on a silica substrate.

A useful process by which this catalyst (and other similar catalysts) can be prepared is set forth in Example III of U.S. Pat. No. 3,746,657. In essence, the method comprises forming a mixture of potassium hydroxide, ammonium molybdate and silica, adding to the mixture phosphoric acid, solutions in nitric acid of the nitrates of cobalt, iron, nickel and bismuth, and more silica to form a slurry, then spray drying and calcining to form the catalyst.

It will readily be appreciated that one of the by-products of this reaction sequence is a large amount of ammonium nitrate especially as molybdenum is usually the major component (in atomic terms) of the finished catalyst and large quantities of ammonium molybdate must therefore be used. This by-product remains in the mixture until the catalyst is subjected to a high temperature treatment at which point it is driven off in the form of ammonia, water vapor and nitrogen oxides. The ammonium nitrate elimination, besides being inconvenient from the point of view of control of the gases eliminated is also very time consuming.

It is found moreover that when placed in an ammoxidation reactor the newly formed catalyst promotes undesirable side reactions for an extended initial period. This undesirable behavior is characterized by an excessive amount of burn of the ammonia reactant, as much as 30–40% of the ammonia being lost in this way.

As a result the reactor has to be operated at somewhat less than peak efficiency until the catalyst has gone through this initial phase of its activity.

It has now been found that by preparing the catalyst in a particular novel way, the difficulties attendant on the ammonium nitrate elimination in the prior art process referred to above are avoided.

Moreover, the catalyst produced in addition to being ready for immediate use at optimum or close to optimum efficiency, has an advantage over catalysts with the same metal ratios but prepared by the prior art process when used in ammoxidation reactions in that it is possible to operate with much closer to the stoichiometric amounts of ammonia and olefin without producing troublesome amounts of by-products.

Additionally, it has been found that, when used to produce acrylonitrile from propylene by an ammoxidation process, the novel catalyst prepared by the process of the invention has demonstrated substantially better results in terms of selectivity to and yield of acrylonitrile over catalysts with the same metal ratios prepared by the prior art process referred to above.

SUMMARY OF THE INVENTION

The present invention provides an (amm)oxidation catalyst prepared by the process which comprises forming an aqueous slurry consisting essentially of the molybdate of at least one of the elements in the group consisting of cobalt, nickel and iron, a bismuth oxide or salt, and optionally a phosphate radical and an ion of an element selected from the group consisting of sodium, potassium and calcium, and thereafter separating the solid phase from the slurry and calcining said solid phase to form the catalyst.

Since a catalyst prepared by this process does not require the elimination of substantial amounts of ammonium nitrate by-product, the calcination treatment is comparatively clean and speedy.

In general, while ammoxidation can be achieved in an ammoxidation process using the catalyst prepared according to the process of the invention with the molybdate of only one or two of the elements cobalt, iron and nickel present with the bismuth oxide or salt, in practice, it is generally preferred that at least two, and more preferably still, all three be present.

This is also convenient since it has been found that the best results are obtained when molybdenum is by far the largest catalytic component in terms of metal atoms in the catalyst. As the molybdenum is incorporated into the slurry from which the catalyst is obtained in the form of a molybdate, it is clear that the more metallic components there are in the slurry in the form of molybdates, the greater will be the ratio of total molybdenum to each of the other catalytic components of the catalyst. Thus, the preferred slurry comprises cobalt, nickel, iron and bismuth in the form of their respective molybdates though in a slightly less preferred form the bismuth can be in the form of an oxide or a salt other than the molybdate.

It is highly advantageous to include in the catalyst a support material which is essentially inactive catalytically but which functions by providing a large surface area for the catalyst and by enabling the catalyst to be used in the highly abrasive environment of a fluidized bed reactor. This support material can be any of those commonly proposed for such use such as, for example, silica, zirconia, alumina and titania. From the point of view of availability, cost and performance silica is usually the preferred support material and is preferably in the form of silica sol for easy dispersion.

While the presence of the phosphate radical and the ion of an element selected from sodium, potassium and calcium is not essential, they nevertheless improve yield and are components of preferred catalysts of the invention. The element selected from sodium, potassium and calcium is most frequently potassium and the phosphate radical and sodium, potassium or calcium ions can be added to the slurry of the molybdates separately or together. Thus the phosphate radical can be added as phosphoric acid or as a metal phosphate such as the phosphate of sodium, potassium or calcium with potassium phosphate being the particularly preferred alternative. In a preferred process the latter mode of addition is used though, if a higher atomic proportion of molybdenum in the catalyst is desired, it is possible to add the sodium, potassium or calcium as the molybdate.

The proportions in which the components of the supported catalyst are present can vary widely but it is usually preferred that the support provides from 30 to 70% such as from 40 to 60% and most preferably about 50% by weight of the total combined weight of the catalyst and the support.

The catalytic elements are preferably present in such amounts that the atomic ratio of molybdenum to any of the other elements present, apart from oxygen, is at least one and more preferably at least two. Preferred catalysts prepared by the process of the invention have the empirical formula:

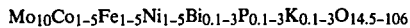
$$Mo_{10}Co_{1-5}Fe_{1-5}Ni_{1-5}Bi_{0.1-3}P_{0.1-3}K_{0.1-3}O_{14.5-106}$$

and still more preferred catalysts have the empirical formula:

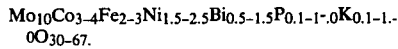
$$Mo_{10}Co_{3-4}Fe_{2-3}Ni_{1.5-2.5}Bi_{0.5-1.5}P_{0.1-1}K_{0.1-1}O_{30-67}.$$

When separated from the slurry the solid phase contains a certain amount of water and it is usually desirable to remove this water by some form of drying process. This can take the form of a simple oven-drying process in which the water containing solid phase is subjected to a temperature that is sufficiently high to vaporize the water and completely dry out the solid phase.

An alternate drying process that is often favored on account of its speed is the so-called spray-drying process in which water-containing solid phase particles are sprayed into contact with hot gas (usually air) so as to vaporize the water. The drying is controlled by the temperature of the gas and the distance the particles travel in contact with the gas. It is generally undesirable to adjust these parameters to achieve too rapid drying as this results in a tendency to form dried skins on the partially dried particles of the solid phase which are subsequently ruptured as water occluded within the particles vaporizes and attempts to escape. By the same token, it is desirable to provide the catalyst in a form having as little occluded water as possible. Therefore, where a fluidized bed reactor is to be used and microspheroidal particles are desired, it is advisable to choose the conditions of spray-drying with a view to achieving complete drying without particle rupture.

The calcination process is usually conducted in air at essentially atmospheric pressure and at a temperature of above about 450° C., such as from about 500° to about 650° C., and preferably at about 550° C. The time to complete the calcination can be anything up to 10 hours, but for most purposes, the calcination need take only from about one to three hours.

The molybdates of the various elements can most conveniently be prepared by double decomposition from ammonium molybdate and the nitrate of the element. This usually results in substantially complete precipitation of the molybdate and by suitable adjustment of the pH and temperature of the solution from which precipitation occurs it is possible to ensure that an insignificant amount of the molybdate is lost and that the precipitate is obtained in dense compact form with a minimum of water of hydration as opposed to gel-like particles with large occlusions of water. The method also ensures that the ammonium nitrate formed is separated with the liquid phase which also contains any unreacted ammonium molybdate. It is possible to provide that all the molybdates be precipitated from the same solution but in such case it is highly desirable that the temperature and pH at which each is precipitated should be controlled as indicated above to yield the precipitate in a dense compact form with a minimum of water of hydration. While this method of making the molybdates is preferred, it is not considered to be the only satisfactory method available.

The catalyst of the invention is particularly useful in the production of acrylonitrile from propylene and in what follows specific reference is made to that process although it should be understood that the described process is also useful for the production of catalysts for ammoxidation of other olefins and for oxidation of aliphatic olefins to aldehydes and acids.

In the most frequently used ammoxidation processes, a mixture of olefin, ammonia and oxygen are fed into a reactor and through a fluidized bed of catalyst deposited on finely divided particles of a support material. The reaction temperature is usually in excess of 400° C. and the pressure is substantially atmospheric. The molar amounts of ammonia and olefin required stoichiometrically are the same, but it is usually necessary to operate with a molar ratio of ammonia to olefin in excess of 1 to reduce the incidence of side reactions.

The catalyst prepared by the process of the invention is particularly well adapted for use in such a process and in what follows its effectiveness and advantages over prior art prepared catalysts are demonstrated in the context of that process.

SPECIFIC EMBODIMENTS

As has been stated above the most preferred form of catalyst consists essentially of the elements given below in the empirical formula indicated:

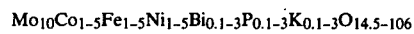
$$Mo_{10}Co_{1-5}Fe_{1-5}Ni_{1-5}Bi_{0.1-3}P_{0.1-3}K_{0.1-3}O_{14.5-106}$$

dispersed on a finely divided silica support which represents from 30 to 70% of the supported catalyst weight. In the experiments that are reported below, specific compositions within this range were chosen to provide the basis for a comparison (Demonstration 1) of the performance of the catalysts produced by the prior art process with those prepared by the process of the invention (Example 1). In Example 2, the production of a somewhat less preferred embodiment of the invention is described and its utility demonstrated in Demonstration 3. Demonstration 2 shows the effectiveness over a prolonged period of a catalyst of the invention prepared by a preferred process.

PRIOR ART PROCESS

A prior art process for the production of a catalyst containing the same elements as that prepared by the process of the invention comprises forming a solution of potassium hydroxide and ammonium molybdate, adding to the solution 60% of the total silica desired in the final composition, adding phosphoric acid to the mixture, followed by solutions in nitric acid of cobalt, iron, nickel and bismuth nitrates and the remainder of the silica. The resulting slurry was then spray-dried and calcined at 550° to 565° C. for two hours, leaving the catalytic elements dispersed on the silica support substantially completely in the form of their oxides. Large volumes of ammonia and nitrogen oxides were driven off during the calcination stage.

In preparing the catalyst by the above process the amounts of reactants were selected to give a finished product with the composition in terms of atomic ratios of essential catalytic elements, of $Mo_{11.1}Co_{4.5}Fe_{3.0}Ni_{2.5}Bi_{1.0}P_{0.19}K_{0.41}$. This catalyst was supported on 50% by weight of the total supported catalyst weight of silica.

In the following Example 1, a catalyst of the invention having a similar composition was prepared using the process of the invention.

EXAMPLE 1

The following molybdates were prepared by double decomposition from ammonium molybdate solution in the manner indicated.

$NiMoO_4$ (62.97 grams)

41.46 grams of molybdenum oxide ($MoO_3$) were dissolved in a mixture of 400 ml of water and 47.5 ml of concentrated ammonia. A solution of 83.75 grams of nickel nitrate hexahydrate in 200 ml of water was added slowly with stirring and the mixture was boiled for approximately two hours.

$CoMoO_4$ (112.93 grams)

77.99 grams of molybdenum oxide were dissolved in a mixture of 717 ml of water and 85.18 ml of concentrated ammonia. A solution of 157.69 grams of cobaltous nitrate hexahydrate in 450 ml of water was added slowly with stirring. The mixture was boiled for almost two hours.

$Fe_2(MoO_4)_3$ (101.15 grams)

73.85 grams of molybdenum oxide were dissolved in a mixture of 678.9 ml of water and 80.66 ml of concentrated ammonia. A solution of 138.17 grams of ferric nitrate monohydrate in 500 ml of water was added slowly at room temperature with stirring.

$Bi_2(MoO_4)_3$ (51.17 grams)

24.61 grams of molybdenum oxide were dissolved in a mixture of 237.7 ml of water and 26.9 ml of concentrated ammonia. A solution of 55.3 grams of bismuth nitrate pentahydrate in 297 ml of water and 20.8 ml of concentrated nitric acid was added with stirring and the pH of the resulting mixture was adjusted to about 6 using ammonium hydroxide.

The mixtures containing the ferric molybdate and the bismuth molybdate were mixed in the same vessel and filtered with suction. The mixtures containing the cobalt and nickel molybdates were likewise mixed and poured through the same filter on top of the ferric and bismuth molybdates.

The combined precipitates were then washed with 1000 ml of water and then transferred to a beaker and slurried with a small amount of water. To this slurry were added 750 grams of a silica sol containing 40% silica and the slurry was stirred.

A solution of 15.75 grams of potassium molybdate pentahydrate dissolved in 65 ml of water was added with stirring and was followed by the dropwise addition of 6.92 grams of 85% phosphoric acid.

The mixture was spray-dried and calcined at 550° C. to produce 600 grams of a catalyst composition with a particle size below 125 microns. The catalyst composition had the essential catalytic elements in the following atomic proportions:

$Mo_{10}Co_{3.41}Ni_{1.9}Bi_{2.26}P_{0.4}K_{0.32}$ and was supported on 50% by weight of the total supported catalyst composition of silica.

EXAMPLE 2

This Example describes the preparation of catalyst according to this invention which does not have the optional potassium, sodium or calcium and phosphate components and in which bismuth is added in the form of an oxide.

The molbydates of nickel, cobalt and iron were prepared according to the method described in Example 1 and were filtered from the solutions from which they were prepared using the same Buchner funnel. In this way 101.15 grams of ferric molybdate, 112.93 grams of cobalt molybdate and 62.97 grams of nickel molybdate were obtained. The combined precipitates were washed with 1000 ml of distilled water and then were slurried with water in a 4000 ml beaker.

Bismuth oxide (26.56 grams) was then added to the slurry followed by 750 grams of a silica sol containing 40% $SiO_2$ and the slurry was thoroughly mixed.

The slurry was finally spray dried and calcined at 750° C. for one hour.

In the above manner 600 grams were obtained of a catalyst composition having the essential catalytic elements in the following proportions:

$Mo_{10}Co_{3.92}Fe_{2.59}Ni_{2.18}Bi_{0.86}$ and comprising 50% by weight of silica support material.

DEMONSTRATION 1

The following table compares the results obtained using both the catalyst prepared by the prior art process (A) and having the essential catalytic elements in the following proportions:

$Mo_{11.1}Co_{4.5}Fe_{3.0}Ni_{2.5}Bi_{1.0}K_{0.41}P_{0.19}$ dispersed on a silica support providing 50% by weight of the catalytic composition, and also a catalyst composition of this invention (B) as described in Example 1. The catalysts were compared using a ½ inch diameter fluidized bed catalytic ammoxidation reactor and the reaction conditions specified.

The prior art prepared catalyst had been calcined for two hours at 550° to 565° C. before use.

TABLE 1

| | CATALYST | | | | | |
|---|---|---|---|---|---|---|
| | $A_1$ | $A_2$ | $A_3$ | $B_1$ | $B_2$ | $B_3$ |
| Temperature °C. | 416 | 417 | 431 | 454 | 430 | 430 |
| Feed % | | | | | | |
| $C_3H_6$ | 8.5 | 8.5 | 8.5 | 8.5 | 8.6 | 8.6 |
| $NH_3$ | 9.4 | 9.4 | 9.4 | 9.3 | 9.3 | 9.3 |
| $O_2$ | 17.2 | 17.2 | 17.2 | 17.2 | 17.2 | 17.2 |
| He | 64.9 | 64.9 | 64.9 | 65 | 64.9 | 64.9 |
| Time (Hrs.) | 0.5 | 20.5 | 45.5 | 1.16 | 20 | 20.5 |
| [1]W/F (g. sec. ml$^{-1}$) | 7.5 | 7.5 | 7.5 | 3.75 | 7.5 | 7.5 |
| Propylene Loading (g/g Cat./hr.) | 0.0766 | 0.0766 | 0.0766 | 0.15 | 0.0766 | 0.0766 |
| Pressure (kg/cm$^2$) | 1.27 | 1.76 | 2.11 | 2.05 | 2.02 | 2.02 |
| [2]Propylene Conversion (%) | 87.4 | 92.3 | 97.1 | 97.8 | 97.9 | 98.1 |
| [3]Acrylonitrile Selectivity (%) | 77.4 | 72.7 | 73.9 | 77.5 | 76.7 | 76.6 |
| [4]Acrylonitrile Yield (%) | 67.5 | 67.0 | 71.8 | 75.8 | 75.0 | 75.1 |
| [5]Yield on Ammonia (%) | 61.0 | 60.5 | 64.9 | 69.9 | 68.8 | 68.8 |
| Effluent $O_2$ | 1.52 | 0.98 | 0.32 | 1.03 | 0.17 | 0.13 |
| $NH_3$ | 0.46 | 0.61 | 0.46 | (trace) | 0.47 | 0.46 |
| $C_3H_6$ | 1.02 | 0.62 | 0.23 | 0.18 | 0.17 | 0.15 |
| CO | 0.39 | 0.61 | 0.83 | 0.88 | 1.17 | 1.19 |
| $CO_2$ | 1.84 | 2.01 | 2.12 | 1.60 | 2.27 | 2.29 |
| $N_2$ | 1.03 | 0.47 | 0.54 | 0.42 | 0.33 | 0.34 |
| HCN | 0.86 | 1.42 | 1.43 | 1.37 | 1.39 | 1.39 |
| (Acrylonitrile) AN | 5.47 | 5.42 | 5.78 | 6.14 | 5.95 | 5.99 |
| (Acetonitrile) ACN | 0.20 | 0.30 | 0.27 | 0.25 | 0.17 | 0.17 |
| (Acrolein) ACR | 0.31 | 0.16 | 0.14 | 0.24 | 0.09 | 0.10 |
| He | Balance up to 100% | | | | | |

NOTES:

[1]W/F is defined as the weight of the catalyst in grams divided by the flow rate of reactants in ml/sec. measured at N.T.P.

[2]Propylene ($C_3H_6$) conversion is defined as: $\dfrac{\text{Mols } C_3H_6 \text{ in feed} - \text{mols } C_3H_6 \text{ in effluent}}{\text{Mols } C_3H_6 \text{ in feed}} \times 100$

[3]Acrylonitrile (AN) selectivity is defined as: $\dfrac{\text{Mols AN in effluent}}{\text{Mols } C_3H_6 \text{ converted}} \times 100$

[4]Acrylonitrile (AN) yield is defined as: $\dfrac{\text{Mols AN formed}}{\text{Mols } C_3H_6 \text{ in feed}} \times 100$

[5]Yield on ammonia ($NH_3$) is defined as: $\dfrac{\text{Mols AN formed}}{\text{Mols } NH_3 \text{ in feed}} \times 100$ As can readily be seen from the above, the catalyst of the invention prepared by my process is substantially better in terms of yield on ammonia, selectivity to and yield on acrylonitrile and gives a slightly better propylene conversion than matured prior art catalyst. In practical terms, this means that the product is cleaner in that less side-reaction products are obtained.

As can be seen from the above, although the catalyst prepared by the prior art process recovers from an initially poor performance, it nevertheless does not reach the level maintained by the catalyst of the invention prepared by my process from the beginning.

DEMONSTRATION 2

This series of experiments demonstrates the constant efficiency of the catalyst prepared by the process set forth in Example 1 over a period of 96 hours.

A catalyst having its essential catalytic elements in the following atomic ratios:

$Mo_{10}Co_{3.47}Fe_{2.3}Ni_{1.94}Bi_{0.77}K_{0.32}P_{0.32}$ and supported on 50% by weight of the total supported catalyst composition of silica was prepared in the same manner as set forth in Example 1.

A reactant flow comprising air, ammonia and propylene in the ratios 10.4:1.1:1.0 at a pressure of 0.98 kg/cm$^2$ was passed over the catalyst at a W/F of 5.0 gm. sec. ml$^{-1}$ and a gas velocity of 10.2 cm/sec.

After 24 hours the reactant ratio was changed to 9.99:1.06:1.0 (air:ammonia:propylene) and this had no substantial effect on the AN yield or selectivity. The results of this series of experiments are set forth in Table 2 following.

TABLE 2

| Time, Hours | 2 | 4 | 5 | 24 | 28 | 29 | 48 | 50 | 53 | 72 | 74 | 77 | 94 | 96 |
|---|---|---|---|---|---|---|---|---|---|---|---|---|---|---|
| Temp, °C. | 432 | 430 | 434 | 433 | 433 | 434 | 437 | 436 | 435 | 437 | 439 | 439 | 440 | 438 |
| GE Conv % | 97.3 | 96.9 | 97.3 | 97.0 | 97.1 | 97.3 | 97.0 | 96.5 | 96.6 | 96.8 | 97.0 | 97.3 | 97.1 | 96.8 |
| AN Select % | 73.8 | 75.3 | 76.0 | 76.0 | 75.3 | 76.2 | 76.9 | 76.4 | 76.6 | 76.2 | 76.4 | 76.5 | 76.8 | 76.6 |
| AN Yield % | 71.8 | 73.0 | 73.9 | 73.8 | 73.1 | 74.1 | 74.6 | 73.8 | 74.0 | 73.8 | 74.1 | 74.4 | 74.6 | 74.2 |
| Yield On $NH_3$ % | 65.3 | 66.4 | 67.2 | 67.1 | 69.0 | 69.9 | 70.4 | 69.6 | 69.8 | 69.6 | 69.9 | 70.2 | 70.4 | 70.0 |
| Eff. Vol % | | | | | | | | | | | | | | |
| $O_2$ | 0.99 | 1.20 | 1.27 | 1.40 | 1.00 | 1.02 | 1.16 | 1.15 | 1.15 | 1.19 | 1.22 | 1.26 | 1.2 | 1.28 |
| $N_2$ | 63.60 | 62.80 | 62.90 | 63.60 | 63.60 | 63.40 | 63.60 | 63.60 | 63.40 | 63.20 | 63.40 | 63.40 | 63.30 | 63.20 |
| CO | 1.28 | 1.20 | 1.15 | 1.12 | 1.08 | 1.08 | 1.02 | 1.00 | 1.01 | 0.98 | 0.99 | 1.00 | 0.97 | 0.94 |
| $CO_2$ | 2.41 | 2.26 | 2.24 | 2.26 | 2.19 | 2.23 | 2.16 | 2.14 | 2.16 | 2.12 | 2.13 | 2.13 | 2.13 | 2.08 |
| $NH_3$ | 0.5 | 0.4 | 0.8 | 0.3 | 0.55 | 0.55 | 0.3 | 0.54 | 0.3 | 0.3 | 0.3 | 0.3 | 0.30 | 0.3 |
| $C_3$ | 0.21 | 0.24 | 0.21 | 0.23 | 0.23 | 0.22 | 0.24 | 0.28 | 0.27 | 0.26 | 0.24 | 0.22 | 0.23 | 0.26 |
| $H_2O$ | 24.10 | 24.20 | 24.40 | 24.40 | 24.40 | 24.60 | 24.60 | 24.40 | 24.50 | 24.60 | 24.70 | 24.80 | 24.80 | 24.70 |
| HCN | 1.57 | 1.54 | 1.54 | 1.68 | 1.60 | 1.60 | 1.71 | 1.73 | 1.82 | 1.66 | 1.64 | 1.64 | 1.61 | 1.61 |
| [1]ACR | trace | trace | trace | trace | 0.06 | 0.04 | 0.04 | 0.04 | 0.04 | 0.08 | 0.08 | 0.08 | 0.08 | 0.08 |
| [2]ACN | 0.33 | 0.25 | 0.25 | 0.25 | 0.25 | 0.21 | 0.21 | 0.21 | 0.21 | 0.20 | 0.20 | 0.20 | 0.20 | 0.20 |

TABLE 2-continued

| ³AN | 5.53 | 5.62 | 5.69 | 5.68 | 5.85 | 5.93 | 5.97 | 5.90 | 5.92 | 5.90 | 5.93 | 5.95 | 5.97 | 5.93 |
|---|---|---|---|---|---|---|---|---|---|---|---|---|---|---|

[1] ACR - Acrolein
[2] ACN - Acetonitrile
[3] AN - Acrylonitrile

DEMONSTRATION 3

The catalyst prepared as described in Example 2 was placed in the ammoxidation reactor used in Demonstration 1.

A gas flow comprising 17.12 vol. % of oxygen, 10.06 vol. % of ammonia and 8.42 vol % of propylene (the balance being helium) was passed through the catalyst bed which was maintained at a temperature of 454° C. The W/F was 3.75 gm. sec. ml$^{-1}$ and the pressure was maintained at 1.05 kg/cm².

After 130 minutes the effluent from the reactor was analyzed and the results indicated that the propylene conversion was 93.9%, the selectivity to acrylonitrile was 73.3% and the acrylonitrile yield was 68.8%.

Thus even without the preferred phosphate and potassium, sodium or calcium components, the catalyst composition of the invention produces results that are comparable with the prior art catalysts incorporating those components.

It can be readily seen from the above comparative data that the catalyst of the present invention produced by my process has substantial advantages over that produced by the prior art process. The relative ease with which the catalyst can be obtained and more significantly the improvement in yield against ammonia are most important. As will be appreciated from the very large volumes of ammonia consumed by the commercial production of acrylonitrile, even a small improvement in the efficiency with which this basic raw material is used will result in very large economics of operation. This invention is therefore of considerable commercial significance.

The above Examples are for the purpose of illustrating the invention only and are not considered as limiting the scope thereof in any way.

It will be obvious to those skilled in the art that it is possible to devise modifications and variations of the invention herein disclosed. Accordingly, it is intended that all such modifications and variations which reasonably fall within the scope of the appended claims are included herein.

I claim:

1. An (amm)oxidation catalyst prepared by the process comprising: forming an aqueous slurry consisting essentially of an oxide or salt of bismuth and the individually prepared molybdate of at least one element selected from the group consisting of cobalt, nickel and iron, and optionally at least one of a phosphate and an ion of an element selected from the group consisting of sodium, potassium, and calcium; separating the solid phase from the slurry, and calcining the solid phase to form the catalyst.

2. A catalyst according to claim 1 in which a finely divided support material is added to the slurry.

3. The catalyst according to claim 1 wherein a silica sol support material is added to the slurry and the calcining of the solid phase is at a temperature above 450° C.

4. An (amm)oxidation catalyst prepared by the process which comprises forming an aqueous slurry containing:
   a. the individually prepared molybdates of cobalt, nickel and iron, and bismuth oxide or salt,
   b. a phosphate radical,
   c. an ion of an element selected from the group consisting of sodium, potassium and calcium adding to the slurry a silica sol support material, separating a solid phase from the slurry and calcining said solid phase at a temperature of from 500° to 650° to form the catalyst.

5. A catalyst according to claim 4 in which the aqueous slurry is formed by mixing an aqueous slurry containing the molybdates of cobalt, nickel and iron and a bismuth oxide or salt with a solution of a phosphate of sodium, potassium or calcium.

6. A catalyst according to claim 4 in which the aqueous slurry contains the molybdate of sodium, potassium or calcium and phosphoric acid.

7. A catalyst according to claim 1 in which the catalytic elements are present in the following atomic ratio:

$$Mo_{10}Co_{1-5}Ni_{1-5}Fe_{1-5}Bi_{0.1-3}$$

8. A catalyst according to claim 4 in which the elements are present in the following atomic ratio:

$$Mo_{10}Co_{1-5}Ni_{1-5}Fe_{1-5}Bi_{0.1-3}P_{0.1-3}K_{0.1-3}$$

dispersed on said silica support material which provides from 30 to 70% of the supported catalyst weight.

9. An (amm)oxidation catalyst prepared by the process comprising forming an aqueous slurry of individually prepared molybdates of cobalt, nickel, iron and bismuth, mixing the slurry with a silica sol and an aqueous solution of potassium phosphate, separating a solid phase from the slurry, spray-drying said solid phase to remove water and calcining the dried solid phase at a temperature above 450° C. to form the catalyst, the above components being added in such proportions that the silica support comprises 30 to 70% of the supported catalyst weight, and the catalyst itself has the empirical formula:

$$Mo_{10}Co_{1-5}Fe_{1-5}Ni_{1-5}Bi_{0.1-3}P_{0.1-3}K_{0.1-3}O_{14.5-106}.$$

* * * * *